(12) United States Patent
Pruitt

(10) Patent No.: US 7,033,317 B2
(45) Date of Patent: Apr. 25, 2006

(54) DISPOSABLE ENDOSCOPE AND METHOD OF MAKING A DISPOSABLE ENDOSCOPE

(75) Inventor: David L. Pruitt, Temecula, CA (US)

(73) Assignee: HydroCision, Inc., Billerica, MA (US)

( * ) Notice: Subject to any disclaimer, the term of this patent is extended or adjusted under 35 U.S.C. 154(b) by 0 days.

(21) Appl. No.: 10/863,874

(22) Filed: Jun. 7, 2004

(65) Prior Publication Data

US 2005/0043589 A1    Feb. 24, 2005

Related U.S. Application Data

(60) Provisional application No. 60/476,474, filed on Jun. 5, 2003.

(51) Int. Cl.
 *A61B 1/04* (2006.01)

(52) U.S. Cl. .................. 600/133; 600/129; 600/176

(58) Field of Classification Search ............... 600/101, 600/129, 133, 169, 176, 175; 359/513, 503, 359/819, 811; 348/335, 340
See application file for complete search history.

(56) References Cited

U.S. PATENT DOCUMENTS

| | | |
|---|---|---|
| 4,392,485 A | 7/1983 | Hiltebrandt |
| 4,580,551 A | 4/1986 | Siegmund et al. |
| 4,706,656 A | 11/1987 | Kuboto |
| 4,784,144 A | 11/1988 | Ono et al. |
| 4,872,740 A | 10/1989 | Terada et al. |
| 4,892,099 A | 1/1990 | Ohkawa et al. |
| 4,911,148 A | 3/1990 | Sosnowski et al. |
| 4,919,112 A | 4/1990 | Siegmund |
| 4,947,827 A | 8/1990 | Opie et al. |
| 5,140,975 A | 8/1992 | Krauter |
| 5,188,092 A | 2/1993 | White |
| 5,241,970 A | 9/1993 | Johlin, Jr. et al. |
| 5,307,803 A | 5/1994 | Matsuura et al. |
| 5,320,602 A | 6/1994 | Karpiel |
| 5,325,845 A | 7/1994 | Adair |
| 5,341,240 A | 8/1994 | Broome |
| 5,397,302 A | 3/1995 | Weaver et al. |
| 5,398,687 A | 3/1995 | Abell |
| 5,416,638 A | 5/1995 | Broome |
| 5,458,112 A | 10/1995 | Weaver |
| 5,519,532 A | 5/1996 | Broome |
| 5,547,457 A * | 8/1996 | Tsuyuki et al. ............. 600/175 |
| 5,549,542 A | 8/1996 | Kovalcheck |
| 5,555,131 A | 9/1996 | Horton |
| 5,599,299 A | 2/1997 | Weaver et al. |
| 5,704,899 A | 1/1998 | Milo |
| 5,779,624 A | 7/1998 | Chang |
| 5,788,681 A | 8/1998 | Weaver et al. |
| 5,834,214 A | 11/1998 | Iovanna et al. |
| 5,843,028 A | 12/1998 | Weaver et al. |

(Continued)

FOREIGN PATENT DOCUMENTS

WO    WO 91/15793    10/1991

(Continued)

*Primary Examiner*—Beverly M. Flanagan
(74) *Attorney, Agent, or Firm*—Buchanan Ingersoll PC

(57) ABSTRACT

An endoscope having a sheath having a plurality of lumens, an imaging bundle received in a first lumen in the sheath, and a lighting bundle received in one or more second lumens in the sheath. A distal tip connects to a distal end of the sheath and includes an objective lens disposed in the distal tip, wherein the objective lens is spaced apart from the distal end of the imaging bundle.

20 Claims, 3 Drawing Sheets

U.S. PATENT DOCUMENTS

| | | |
|---|---|---|
| 5,892,630 A | 4/1999 | Broome |
| 5,916,147 A | 6/1999 | Boury |
| 5,938,585 A | 8/1999 | Donofrio |
| 5,960,145 A | 9/1999 | Sanchez |
| 6,010,449 A | 1/2000 | Selmon et al. |
| 6,013,024 A | 1/2000 | Mitsuda et al. |
| 6,099,485 A | 8/2000 | Patterson |
| 6,146,389 A | 11/2000 | Geitz |
| 6,184,923 B1 * | 2/2001 | Miyazaki ............. 348/75 |
| 6,213,974 B1 | 4/2001 | Smith et al. |
| 6,217,510 B1 | 4/2001 | Ozawa et al. |
| 6,277,065 B1 | 8/2001 | Donofrio |
| 2002/0099267 A1 * | 7/2002 | Wendlandt et al. ......... 600/173 |
| 2002/0186478 A1 * | 12/2002 | Watanabe et al. .......... 359/819 |
| 2004/0143162 A1 * | 7/2004 | Krattiger et al. ............ 600/175 |
| 2005/0014996 A1 * | 1/2005 | Konomura et al. ......... 600/175 |

FOREIGN PATENT DOCUMENTS

| | | |
|---|---|---|
| WO | WO 93/15647 | 8/1993 |
| WO | WO 98/01074 | 1/1998 |
| WO | WO 00/54653 | 9/2000 |

* cited by examiner

DISPOSABLE ENDOSCOPE AND METHOD OF MAKING A DISPOSABLE ENDOSCOPE

CROSS REFERENCE TO RELATED APPLICATION

This application claims priority to U.S. Provisional Patent Application No. 60/476,474, filed Jun. 5, 2003, which is incorporated herein by reference in its entirety.

BACKGROUND OF THE INVENTION

Endoscopes are expensive pieces of surgical equipment which are difficult to clean and sterilize between different patients. Moreover, endoscopes contain fiber optic bundles of lighting and imaging fibers which are rather fragile. Therefore, a problem that is common to endoscopes is that they break easily, especially when being cleaned and sterilized. For example, a typical lifetime is only about ten uses when re-using uretroscopic endoscopes.

What is desired, therefore, is an endoscope which can be manufactured much more inexpensively than is possible with current designs. Specifically, the need exists for an endoscope which can be made so inexpensively (e.g.: by reducing both its component costs and manufacturing steps) that it would be disposable.

SUMMARY OF THE INVENTION

In one aspect of this invention, an endoscope, including a sheath having a plurality of lumens; an imaging bundle received in a first lumen in the sheath; a lighting bundle received in one or more second lumens in the sheath; a distal tip connected to a distal end of the sheath; and an objective lens disposed in the distal tip, wherein the objective lens is spaced apart from the distal end of the imaging bundle.

In another aspect of this invention, a method of forming an endoscope, including the steps of providing a sheath having a plurality of lumens; inserting an imaging bundle into a first lumen; inserting a lighting bundle into one or more second lumens; simultaneously cutting the distal ends of the sheath and the imaging and lighting bundles; and attaching a distal tip over the distal end of the sheath, the distal tip comprising an objective lens, wherein the distal tip is spaced apart from the distal ends of the imaging and lighting bundles.

BRIEF DESCRIPTION OF THE DRAWINGS

The invention will now be described in greater detail with reference to the preferred embodiments illustrated in the accompanying drawings, in which like elements bear like reference numerals, and wherein.

DESCRIPTION OF THE INVENTION

Figure 1:
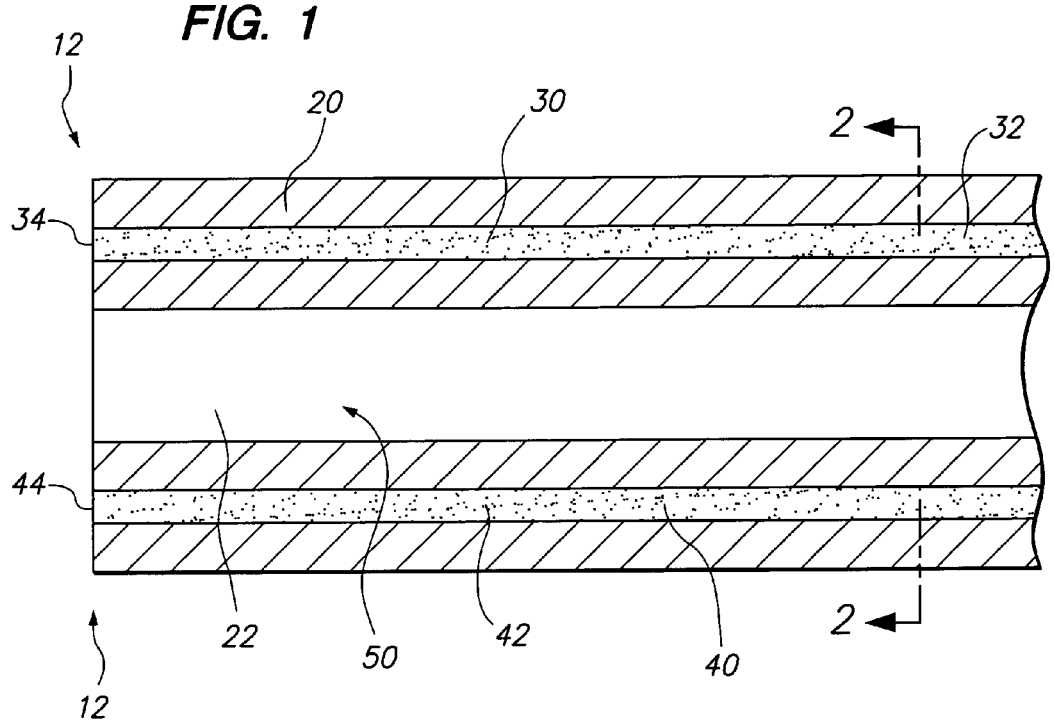
FIG. 1 is a sectional view of the distal end of a sheath, with lighting and imaging fiber bundles passing therethrough, prior to attaching a novel clear distal tip, in accordance with the present invention. (Corresponding to line 1—1 in FIG. 2).
Figure 2:
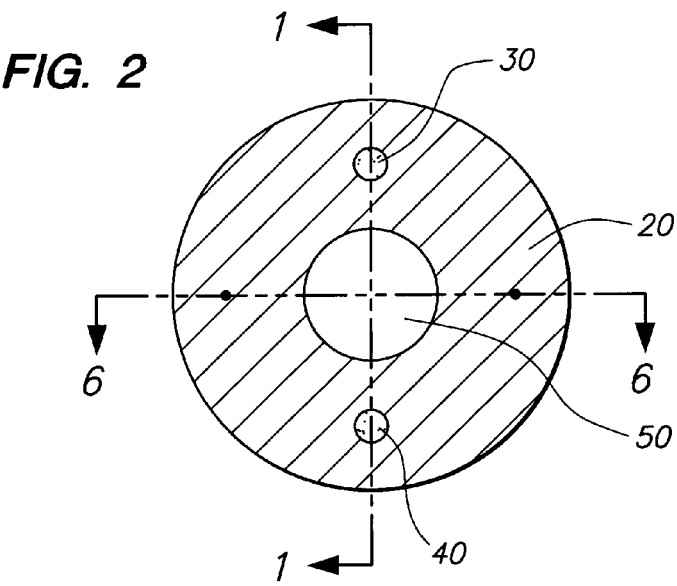
FIG. 2 is a sectional view taken along line 2—2 in FIG. 1.

FIGS. 1 and 2 show the sheath 20/fiber bundles 30, 40 of the present endoscope 10. In this example, the sheath 20 has three lumen 22, 32, 42 passing therealong. It is to be understood that sheaths 20 having additional (or fewer) lumen are also encompassed by the present invention. As can be seen in FIG. 2, a fiber optic lighting bundle 30 is received in a first lumen 32 and a fiber optic imaging bundle 40 is received in a second lumen 42. The third lumen 22 is left open and functions as a large central working channel 50.

Figure 3:
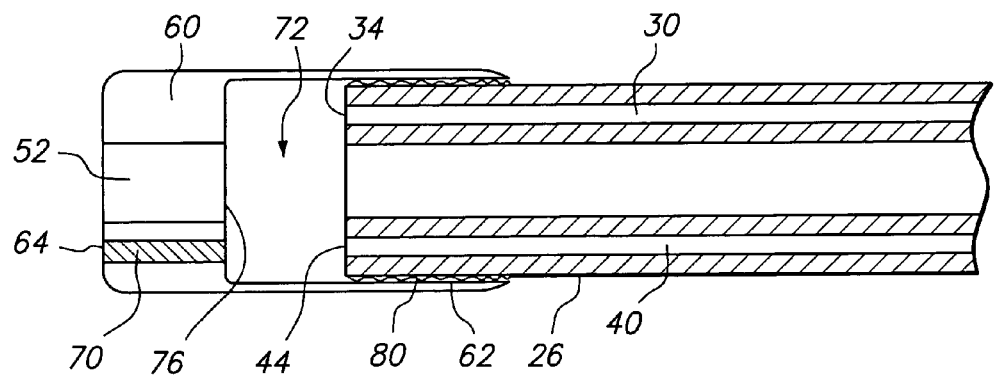
FIG. 3 shows the attachment of the clear distal tip to the sheath/fiber bundle structure of FIG. 1.

In a preferred method of making the present invention, the system of FIGS. 1 and 2 is first assembled, and thereafter the distal tip 60 shown in FIG. 3 is attached. For reasons that will be explained, the distal tip 60 shown in FIG. 3 will preferably be made of a light transmitting or more preferably "clear" material. Exemplary light transmitting materials include glass and plastic. It is to be understood, however, that the present invention also encompasses embodiments in which the distal tip 60 is not clear, with light instead passing through a lumen in the distal tip 60.

An advantage of manufacturing the present system by first assembling the components of FIGS. 1 and 2, and then attaching the clear distal tip 60 of FIG. 3 is as follows.

As can be seen in FIG. 1, very long sections of sheath 20 can be made with imaging 40 and lighting bundles 30 pre-fit therein. Then, these very long sections of sheath 20/fiber bundles 30, 40 can be cut into individual endoscopes 10 of desired lengths. At the time of this cutting, both the sheath 20 and the fiber (lighting and imaging) bundles 30, 40 disposed therein will be cut cleanly together at its distal end 12. By cutting the sheath 20 together with its imaging and lighting bundles 40, 30 at the same time, (as a single unit), the distal ends 12 of the imaging and lighting bundles 40, 30 will be polished when they are cut. If the bundles 30, 40 are plastic, the cutting and polishing may be done with a hot wire. Alternatively, if the bundles 30, 40 are glass, they can be simultaneously cut, ground and polished.

Figure 4:
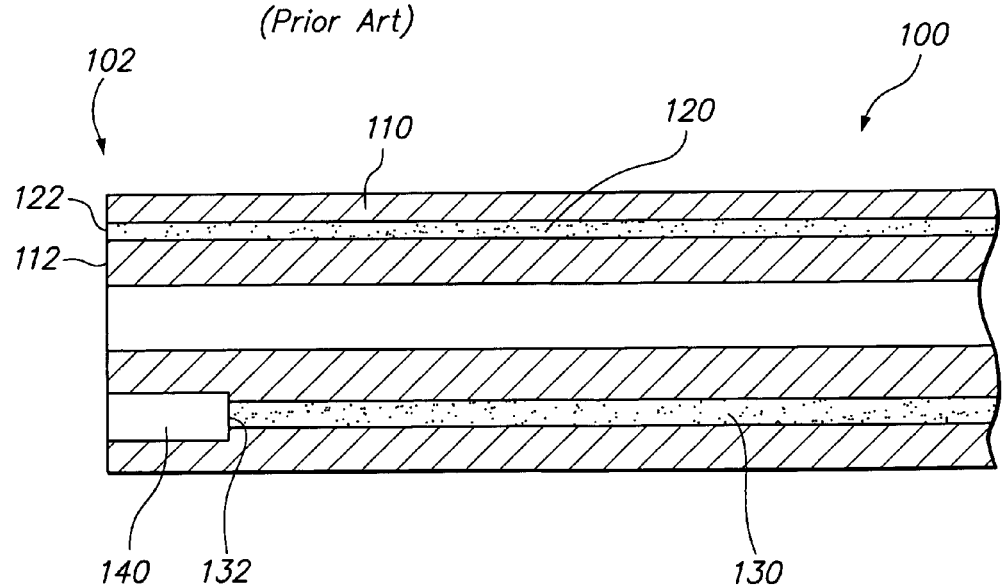
FIG. 4 is a sectional view of the distal end of a common pre-existing endoscope design.

A result of performing a single cut through the sheath 20 and its imaging and lighting bundles 40, 30 results in the distal ends 12 of these three elements all being co-planar to one another. In contrast, pre-existing endoscopes 100 did not have the distal ends 102 of the imaging and lighting bundles 130, 120 disposed co-planar to one another. This was due to the fact that an objective lens 140 needs to be attached to the distal end of the imaging bundle 130. (An example of such a pre-existing system is shown in FIG. 4.)

Thus, systems of manufacturing these pre-existing endoscopes 100 did not cut/polish the ends of the imaging and lighting bundles 120, 130 together as is conveniently accomplished by the present invention. Rather, these common pre-existing endoscopes 100 were assembled by first cutting the sheath 110 to a desired length, and then separately cutting and polishing the distal ends 132, 122 of the imaging and lighting bundles 130, 120, slipping a ferrule (metal ring) around the distal end 132 of the imaging bundle 130 and then inserting each of the imaging and lighting bundles 130, 120 into separate lumens in the sheath 110. As such, the ferrule is used to connect the lens 140 and the distal end 132 of the imaging fiber 130 together. This approach was time consuming. First, since the sheath 110 and each of the lighting and imaging bundles 120, 130 were separately cut and finished. Second, since the lighting and imaging bundles 120, 130 were separately advanced through lumens in the sheath 110. Third, since the distal ends 112, 122, 132 of the sheath 110 and lighting and imaging bundles 120, 130 had to be aligned.

The present invention is thus able to simplify manufacturing steps considerably by positioning the distal ends 44, 34 of the imaging and lighting bundles 40, 30 co-planar to one another. In accordance with a preferred aspect of the invention, the objective lens 70 is positioned in alignment with, and distal to, the imaging bundle 40 without the distal end 34 of the lighting bundle 30 having to be co-planar with the distal end 74 of the objective lens 70 (as in FIG. 4), by instead using a novel "clear tip" distal end 60, as follows.

Referring to FIG. 3, a "clear" distal tip 60 is received over the distal end 12, of components FIGS. 1 and 2. This distal tip 60 may preferably be made from glass, or more preferably, from plastic.

A first advantage of the distal tip 60 being made of a clear material is that light from the end of the lighting bundle 30 will diffuse therethrough such that the target tissue will be illuminated even though the distal end 34 of the lighting bundle 30 is positioned proximally (i.e. upstream) of the distal end 74 of the objective lens 70. Moreover, depending on the specific material used to make the clear distal tip 60, the light exiting the lighting bundle 30 may diffuse widely, thereby illuminating a larger tissue surface area than could be accomplished with a pre-existing system as shown in FIG. 4 where the distal end 122 of the lighting bundle 120 and the objective lens 140 are co-planar. Moreover, materials having a higher index of refraction could potentially exhibit more diffuse lighting therethrough, thus illumination a greater tissue surface area.

A second advantage of the present distal tip 60 is that it can be pre-fitted with the objective lens 70 therein. (This advantage is true even if the distal tip 60 is not made of a clear material). As such, there is no need to attach, or otherwise position, the objective lens 70 to the distal end 44 of the imaging bundle 40 (as was done, for example in the prior art system seen in FIG. 4). A disadvantage of the approach seen in the pre-existing system of FIG. 4 is that, by gluing the objective lens 140 to the imaging bundle 130, partial or complete lens separation from the imaging bundle 130 can occur. Such lens 140 separations tend to disrupt the picture, most notably by producing rainbow effects.

Therefore, the lens 70 would preferably be mounted into the distal tip 60 with an appropriate anti-reflective coating to assure optimal image transmission. Alternatively, the lens 70 and tip carrier could be could be made as separate components and then assembled into the distal tip 60.

A third advantage of the system shown in FIG. 3 is that an air space "gap" 72 is preferably provided between the distal end 44 of the imaging bundle 40 and the proximal end 76 of the objective lens 70. This feature is not seen in any pre-existing system. It offers many advantages. For example, the bending stresses in the imaging bundle 40 are not transmitted to the objective lens 70 at all. Moreover, frequencies of light which may cause the imaging (and lighting) bundles 40, 30 to overheat would not necessarily cause the objective lens 70 to overheat, since heat from the bundle(s) 30, 40 would not be conducted directly into the lens 70, due to the presence of the "air gap" 72. Furthermore, the advantageous use of an "air gap" 72 between the distal end 44 of the imaging bundle 40 and the proximal end 76 of the lens 70 would still be advantageous even in those embodiments in which the distal end 32 is not clear (i.e.: in which light from the lighting bundle 30 instead passes through a lumen in the distal tip 60).

A fourth advantage of the present clear tip design is that it can be easily attached to the distal end 12 of the endoscope 10. For example, a thin layer of adhesive 80 can be provided between the inner surface 62 of the clear tip 60 and the outer surface 26 of the sheath (FIG. 3). Any medically acceptable adhesive that will not damage the optical surface of the instrument is potentially of use in the invention. In one embodiment, this thin adhesive layer 80 can be made from a UV curable adhesive, for example a UV-curable epoxy adhesive. Thus, when the distal end 12 of the endoscope 10 is exposed to UV light, the epoxy will "cure". A distinct advantage of the present clear tip design is that such UV light will simply pass through the tip 60 and reach the epoxy disposed thereunder. Thus, the present epoxy can be cured by UV light although it is positioned between two separate components of the system. This advantageously reduces manufacturing steps and their associated costs. Another useful feature of the design as shown is that the adhesive 80 is not in the light path, minimizing potential interference of the adhesive 80 with image quality or brightness. It can be appreciated that any suitable adhesive 80, which can reliably adhere the tip 60 to the outer surface 26 of the sheath 20 can be used.

Alternatives to adhesives 80 can also be used. In particular, sonic or heat welding can join parts, especially plastic parts. The use of detents or other mechanical interlocks is possible, but might raise costs. Interference fits are possible, but it will generally be better to supplement such contacts with adhesive, for safety.

A fifth advantage of the clear tip 60 is that it can be made of a material which only passes selective wavelengths of light therethrough. This can be advantageous when using therapeutic compounds which are activated by specific frequencies of light.

In addition, the clear tip is preferably constructed optionally with lenses to focus and distribute the illuminating light in the area, which is imaged by the imaging lens.

It is expected that the time and energy saved by: (1) simultaneously cutting the sheath 20 length while polishing the distal ends of the imaging and lighting bundles 40, 30, and then simply (2) attaching the clear tip 60 to the distal end 12 of structure, will result in an endoscope 10 which can be manufactured inexpensively enough that it is disposable.

Figure 5:
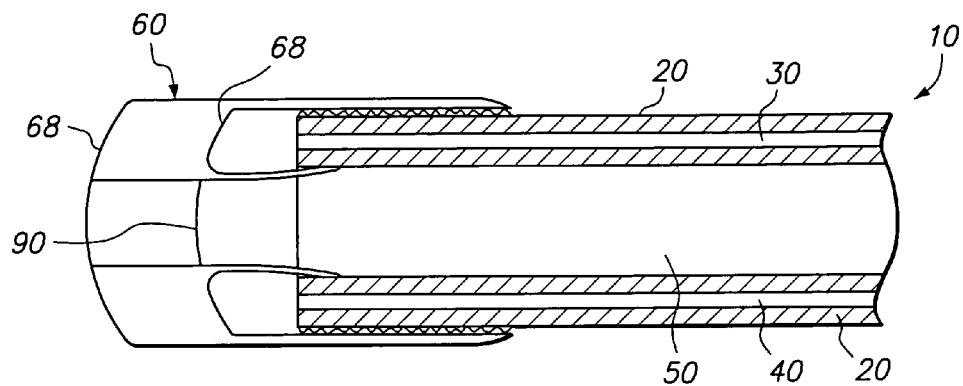
FIG. 5 is a sectional view of an alternative embodiment of the distal tip.

An alternative shape of the tip 60 is shown in FIG. 5. As shown in FIG. 5, the tip 60 has curved surfaces 68 in it, so it can act as a lens, especially for the imaging fiber bundle 40. Such surfaces 68 can be cast integrally with the tip 60 during its manufacture, for example by injection molding. As shown, the surfaces 68 are simple curves, but aspheric surfaces may be preferred so as to focus as much light as possible on the entrance pupil of the fiber bundle 30, 40. If required, a corresponding aspheric could be positioned at the exit of the fiber bundle 30, 40 to reshape the image.

A second alternative feature also shown in FIG. 5 is a projection rim 90 that fits inside the central working lumen 50. Either by closeness of fit, or by virtue of adhesive for a reliable seal, the rim 90 seals the empty optical space so that fluid cannot get into the optical path during the procedure.

As can be seen in FIG. 3, the clear tip 60 also has a central working channel 52 passing therethrough, which can be placed in alignment with the working channel 50 of the sheath 20, permitting tool or irrigation access therethrough.

As illustrated in FIG. 3, the distal tip 60 may be cylindrical. More preferably, the distal end 64 of the distal tip 60 can be beveled or curved to minimize the potential for tissue trauma as the endoscope 10 is advanced into the patient.

Figure 6:
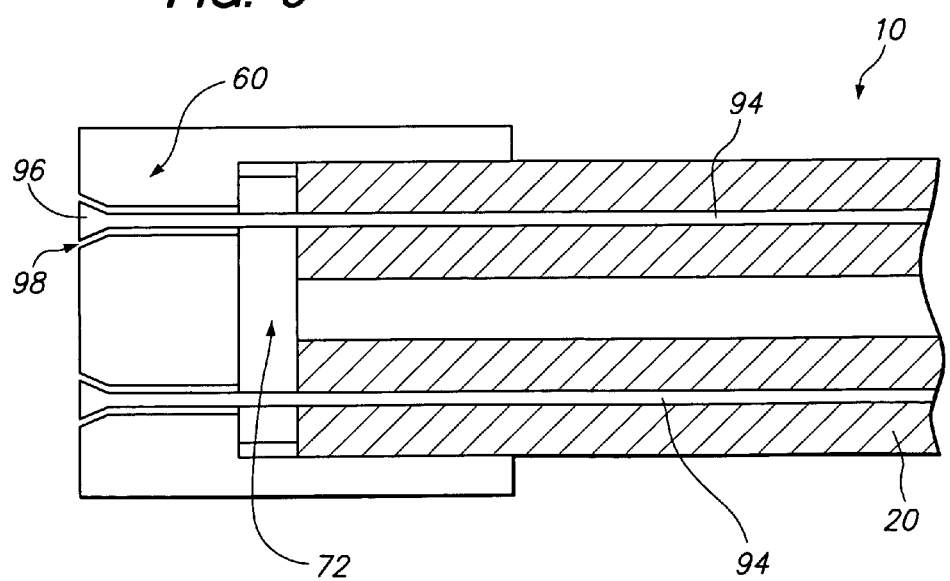
FIG. 6 is a sectional view taken along line 6—6 in FIG. 2 showing an optional embodiment of the present invention with pull wires passing through the distal tip.

Lastly, FIG. 6 shows an embodiment of the present invention corresponding to a view taken along line 6-6 in FIG. 2, showing optional pull wires 94 passing through the distal tip 60. The drawing illustrates a useful design option that can simplify assembly. Here, a funnel-shaped 98 feature in the distal tip 60 retains the pull wire 94. The wires 94 can be threaded into the endoscope 10 after the distal tip 60 is bonded in place, simplifying assembly. Moreover, the application of force to pull wires 94 will tend to pull the tip 60 against the distal sheath 20. In another embodiment, the funnels 98 in FIG. 6 can be deeper, so that the bead 96 on the pull wire 94 is essentially retained by the mechanically strong sheath 20. Alternatively, the pull wires 94 can be inserted in such a slot in the sheath 20, and then the tip 60, optionally lacking openings for pull wires 94 would be bonded in place.

The endoscope 10 has been illustrated with two pull wire lumens 16, a working lumen 52, and one lumen 32, 42 each for lighting and imaging. This is a minimal configuration, and embodiments having more lumens are within the scope of the invention. For example, there could be three or four pull wire lumens 16, and two or three lighting lumens, for example as shown in U.S. Pat. No. 6,458,076, by the same inventor.

While this invention has been described with reference to the preferred embodiments described above, it will be appreciated that the configuration of this invention can be varied and that the scope of this invention is defined by the following claims.

The invention claimed is:

1. An endoscope, comprising:
   a sheath having a plurality of lumens, the sheath comprising:
     an imaging bundle received in a first lumen in the sheath; and
     a lighting bundle received in one or more second lumens in the sheath, and wherein distal ends of the imaging bundle, the lighting bundles and the sheath are disposed in the same plane;
   a distal tip connected to the distal end of the sheath;
   an adhesive layer disposed between the sheath and the distal tip; and
   an objective lens disposed in the distal tip, wherein the objective lens is spaced apart from the distal end of the imaging bundle.

2. The endoscope of claim 1, wherein the distal tip material is glass or plastic.

3. The endoscope of claim 2, wherein the distal tip is made of a light transmitting material.

4. The endoscope of claim 3, wherein the light transmitting material is a clear material.

5. The endoscope of claim 1, wherein the sheath has a working channel lumen.

6. The endoscope of claim 1, wherein the adhesive layer comprises a UV curable material.

7. The endoscope of claim 1, wherein the distal tip is generally cylindrical in shape.

8. The endoscope of claim 1, wherein the distal tip has curved or beveled edges.

9. The endoscope of claim 1, wherein the distal tip has curved surfaces configured to act as a lens.

10. The endoscope of claim 1, wherein the lens has an aspheric surface.

11. The endoscope of claim 1, further comprising pull wires passing through lumens in the sheath, wherein the pull wires are connected to the distal tip.

12. The endoscope of claim 1, further comprising pull wires passing through lumens in the sheath, wherein the pull wires are not connected to the distal end of the sheath.

13. The endoscope of claim 1, further comprising pull wires connected to the distal end of the sheath.

14. The endoscope of claim 13, wherein the pull wires are not connected to the inside of the distal tip.

15. A method of forming an endoscope, comprising:
   providing a sheath having a plurality of lumens;
   inserting an imaging bundle into a first lumen;
   inserting a lighting bundle into a second lumen;
   simultaneously cutting a distal end of the sheath and the imaging and lighting bundles; and
   attaching a distal tip over the distal end of the sheath, the distal tip comprising an objective lens, wherein the distal tip is spaced apart from the distal ends of the imaging and lighting bundles.

16. The method of claim 15, wherein the distal ends of the imaging and lighting bundles are disposed in the same plane.

17. The method of claim 15, wherein the distal tip is made of a light transmitting or clear material.

18. The method of claim 15, wherein the distal tip is attached to the distal end of the sheath by activating a curable epoxy layer disposed between distal end of the sheath and the distal tip.

19. The method of claim 15, wherein the distal tip is attached to the distal end of the sheath by activating a curable epoxy layer disposed between a distal end of the sheath and the distal tip.

20. The method of claim 19, wherein the curable epoxy layer is cured by exposure to UV light.

* * * * *